United States Patent [19]

Lamm

[11] Patent Number: 4,777,293

[45] Date of Patent: Oct. 11, 1988

[54] METHOD FOR THE SYNTHESIS OF PHARMACOLOGICALLY ACTIVE COMPOUNDS AND INTERMEDIATES FOR SUCH SYNTHESIS

[75] Inventor: Bo R. Lamm, Göteborg, Sweden

[73] Assignee: Aktiebolaget Hassle, Molndal, Sweden

[21] Appl. No.: 753,682

[22] Filed: Jul. 10, 1985

[30] Foreign Application Priority Data

Aug. 13, 1984 [SE] Sweden .............................. 84040732

[51] Int. Cl.$^4$ ................. C07C 93/06; C07D 209/04; C07D 417/04
[52] U.S. Cl. ............................... 564/349; 544/134; 548/503
[58] Field of Search .................. 564/349; 544/134; 548/503

[56] References Cited

U.S. PATENT DOCUMENTS

3,729,461  4/1973  Pomeranz et al. .................... 536/1
4,207,413  6/1980  Szarek et al. ........................ 536/1

FOREIGN PATENT DOCUMENTS

1598667  3/1978  United Kingdom .

OTHER PUBLICATIONS

Chem. Abstr. 93 Abstr. #94935D (1980).
John W. Green, Carbohydrates Chemistry and Biochemistry, 2d Ed., vol. 1B, ed. Ward Pigman & Derek Horton, 1980, p. 1144.

*Primary Examiner*—Nicky Chan
*Attorney, Agent, or Firm*—Brumbaugh, Graves Donohue & Raymond

[57] ABSTRACT

A process for the preparation of an aryloxypropanolamine of the formula

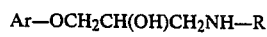

I wherein Ar is a carbocyclic or heterocyclic aromatic group and R is an alkyl or substituted alkyl group having 1 to 6 carbon atoms, characterized in subjecting a compound of the formula

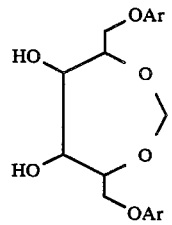

II to oxidative cleavage to a dialdehyde of the formula

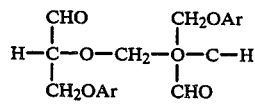

III which is then made subject to reduction, amination, acetal hydrolysis, and, where required, removal of a nitrogen protective group, to the formation of a compound of formula I, or an acid addition salt thereof, a compound of formula II and the preparation thereof from mannitol.

6 Claims, No Drawings

METHOD FOR THE SYNTHESIS OF PHARMACOLOGICALLY ACTIVE COMPOUNDS AND INTERMEDIATES FOR SUCH SYNTHESIS

DESCRIPTION

Technical field

The present invention relates to a method for the preparation of β-receptor blocking aryloxyhydroxypropylamines and to intermediates for the preparation of said compounds.

BACKGROUND OF THE INVENTION

β-receptor blocking agents such as propranolol,

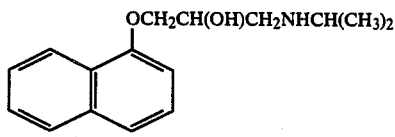

alprenolol,

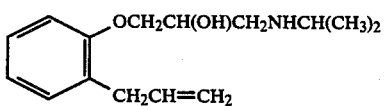

and metoprolol,

have been shown to possess good therapeutic effects in treating heart diseases and vascular diseases, such as angina pectoris, hypertonia, vasoregulatorial neurasthenia and certain forms of arrhythmia.

The pharmacologically active form of the above-mentioned and other β-receptor active agents have the S configuration, and methods for the synthesis of such compounds in enantiomerically pure form are clearly valuable.

Of the various methods available for the synthesis of individual enantiomers, some are based upon the use of optically active natural products such as carbohydrates. In the case of the above-mentioned B-receptor active agents, methods for their synthesis from the naturally occuring alditol, D-mannitol, have been described e.g. in GB 1 598 667 and GB 1 598 668. All these methods start with cleavage of the $C^3-C^4$-bond of 1,2:5,6-di-O-isopropylidene-D-mannitol with periodate or lead tetraacetate. The isopropylidene-protected D-glyceraldehyde is, however, an unstable compound that rapidly undergoes decomposition. Its water solubility poses additional problems in the isolation.

DISCLOSURE OF THE INVENTION

The present invention is related to a process for the preparation of an aryloxypropanolamine of the formula Ar-OCH₂CH(OH)CH₂NH-R     I wherein Ar is a carbocyclic or heterocyclic aromatic group and R is an alkyl group having 1 to 6 carbon atoms which may be substituted. The process is characterized in subjecting a compound of the formula

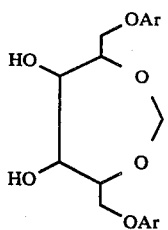

to oxidative cleavage to a dialdehyde of the formula

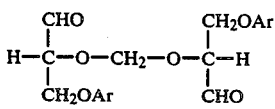

To facilitate cleavage of the $C^3C^4$-bond, free hydroxy groups may advantageously be protected by esterification or etherification. The dialdehyde of formula III is then made subject to reduction, amination, acetal hydrolysis and, where required, removal of a nitrogen protective group to the formation of a compound of formula I or an acid addition salt thereof.

The groups Ar and R are selected to produce a beta-receptor-active compound of formula I.

A carbocyclic aromatic group Ar may be i.a. a naphthyl group or a phenyl group substituted in the 4 and/or 2 position with a hydroxyl group, an alkyl, alkenyl, alkoxyalkyl, alkoxy, alkenyloxy, alkoxy- -alkoxy, alkylcarbonyl, alkylcarbamoyl, carbamoylalkyl or alkylcarbamoylalkyl group containing 1 to 4 carbon atoms in each alkyl or alkenyl part, or a halogen atom. Examples of carbocyclic aromatic groups Ar include 1-naphthyl and phenyl substituted with 4-hydroxy, 2-allyl, 4-methoxyethyl, 4-(2-cyclopropylmethoxyethyl), 4-(2-cyclopropylmethoxyethoxy),4-methoxy, 2-allyloxy, propylcarbamoyl, acetyl and carbamoylmethyl.

A heterocyclic aromatic group Ar may be i.a. a 4-indol group or a 4-morpholino-2,1,3-thiodiazol-5-yl group.

Examples of alkyl groups R include isopropyl and tert. butyl.

Examples of substituted alkyl groups R include 2-(3,4-dimethoxyphenyl)ethyl 2-(N,N-dialkylureido)ethyl, 2-morpholincarboxamido-ethyl, and possibly OH-substituted 4-OH-piperidinecarboxamido-ethyl.

Beta-receptor-active compounds that can be synthesized according to the above process, include acebutolol, alprenolol, atenolol, betaxolol, celiprolol, diacetolol, metoprolol, nadolol, oxprenolol, pindolol, prenalterol, propranolol and penbutolol.

Stoichiometrically the above process would produce two equivalents of compound I for each equivalent of compound II or III. Compound I contains a chiral centre at the 2-carbon of the propyl chain. Compounds II and III each contain two corresponding chiral centres.

According to the present invention it has been found that the compound of formula II may advantageously be obtained in enantiomerically substantially pure form from enantiomerically substantially pure mannitol, as will be further described below. Thus, according to a preferred embodiment the invention is related to employing an enantiomerically substantially pure compound of formula II in the process described above, which produces the compound of formula I as a substantially pure enantiomer.

As described above, the S-form of a compound of formula I is usually the preferred form. According to a particularly preferred embodiment of the present invention the compound of formula II is used as the D-isomer to produce the compound of formula I in S-form. The D-isomer is obtainable from D-mannitol as will be described below.

Oxidative cleavage of the compound of formula II to produce the compound of formula III may be done by means of an oxidizing agent such as sodium periodate or lead tetraacetate.

The reduction, amination, acetal hydrolysis and, where required, removal of a nitrogen protective group, producing a compound of formula I from the compound of formula III is preferably carried out by the following route

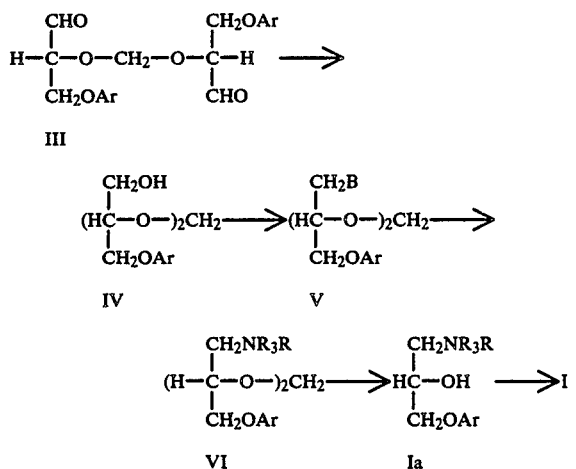

Reduction of the dialdehyde (III) gives a diol (IV), which is activated by introduction of a leaving group B, such as a halogen or sulfonic acid residue, preferably a methanesulfonic acid residue to the formation of compound V which is allowed to react with an amine $HNR_3R$, wherein $R_3$ is hydrogen or a nitrogen protective group that can be subsequently removed, such as a benzyl or substituted benzyl group and R is as defined above, to the formation of the amine VI, followed by acidic removal of the methylene bridge. When $R^3$ is a nitrogen-protective group, this group is finally removed to the formation of the end compound I. Alternatively the conversion of V to I is carried out via the route

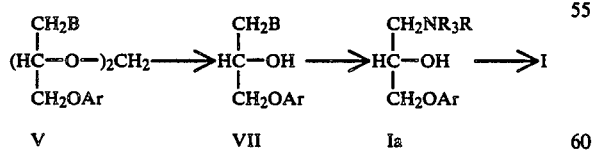

The acetal V is hydrolyzed to the sec. alcohol VII which is aminated and, where required, deprotected to form the end compound I.

Other feasible routes are reductive amination of the dialdehyde III to form the diamine VI from which compound I is formed by hydrolysis; or hydrolysis of the dialdehyde III followed by reductive amination.

In a further aspect the present invention is related to the compound of the formula

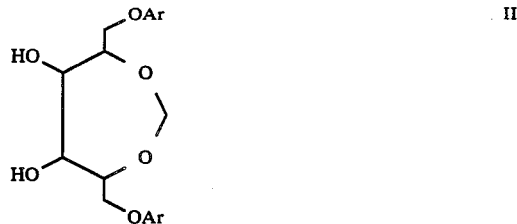

wherein Ar is an aromatic group as defined above, which compound is useful as an intermediate in the preparation of compounds of formula I above.

In accordance with what is stated above, an enantiomerically substantially pure form of compound II is preferred. Particularly preferred is the D form of the compound of formula II derived from D-mannitol.

Compound II in D form may be obtained from D-mannitol along the synthesis route

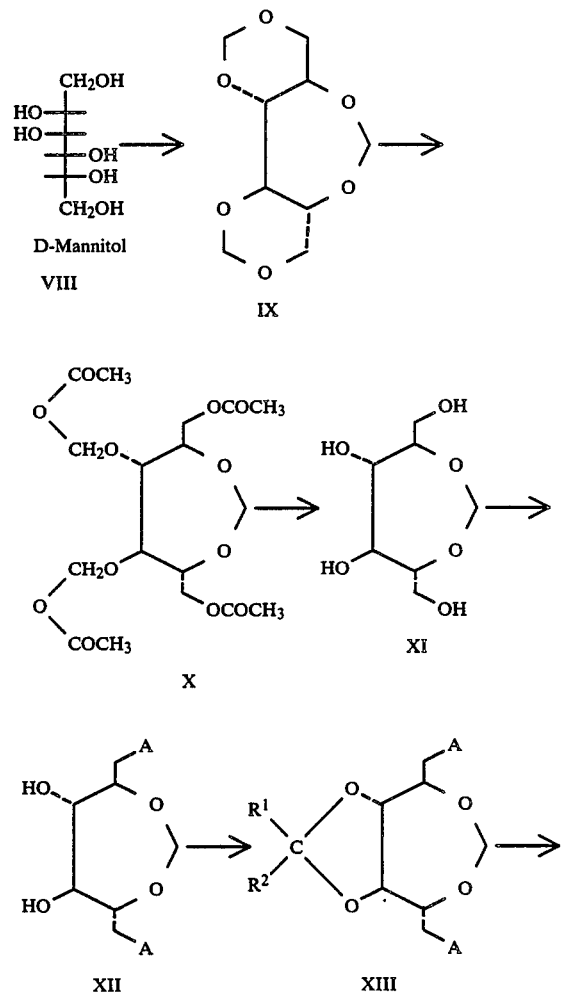

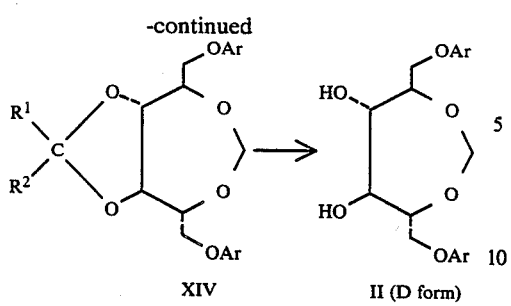

D-mannitol VIII is allowed to react with aqueous formaldehyde and conc. hydrochloric acid to yield 1,3:2,5:4,6-tri-O-methylene-D-mannitol (IX), which in two steps, acetolysis and methanolysis, is converted into 2,5-O-methylene-D-mannitol (XI). A leaving group A, e.g. a sulfonic acid residue, a halogen or a phosphorus-containing group, is introduced to the formation of a compound of formula XII. Thus, treatment of compound XI with slightly more than the theoretical amount of a sulfonyl chloride gives the 1,6-disulfonate. The di-p-toluenesulfonate is described in the literature (Baker, S.B. Can. J. Chem. 31 (1953) 821).

The remaining two hydroxy groups in positions 3 and 4 are next blocked by suitable protective groups or a common protective group

which must resist the next step, nucleophilic replacement of the sulfonate groups in position 1 and 6 by aryloxy groups ArO-, but on the other hand, the protecting group(s) must be removable without simultaneously removing the 2,5-O-methylene bridge. An extensive compilation of protective groups may be found in Greene, T. W. "Protective Groups in Organic Synthesis", Wiley 1981.

In the protective group $R^1R^2C<$, $R^1$ and $R^2$ may be the same or different entities. If the same, then they can be alkyl having 1 to 4 carbon atoms or alkoxy having 1 to 4 carbon atoms. If they are different, $R^1$ may be H, alkyl having 1 to 4 carbon atoms, or alkoxy having 1 to 4 carbon atoms; $R^2$ may be alkyl having 1 to 4 carbon atoms, alkoxy having 1 to 4 carbon atoms, or aryl. In addition $R^1R^2C<$ may represent a ring such as cyclopentylidene, cyclohexylidene, or cycloheptylidene. Furthermore $R^1R^2C<$ be replaced by silicon-containing protective groups such as trimethylsilyl or dimethylsilylene.

In the present case, the methoxymethylene group appears most suitable, since it can be introduced with the aid of the relatively inexpensive trimethyl orthoformate and it can be removed under mild conditions. Homologues of methoxymethylene, orthocarbonates, acetals and ketals, and silicon-containing groups such as trimethylsilyl or dimethylsilylene are also useful. It should be noted that 3,4-O-benzylidene-1,6-di-O-p-toluenesulfonyl-D-mannitol is a known compound (Lloyd, W. J. and Harrison, R. Carbohydr. Res. 26 (1973) 91). The ditosylate XII gives an easily purified, crystalline methoxymethylene compound XIII.

Introduction of the aryloxy groups and 3,4-deprotection yields the vic.-diol II.

The process for preparing compound II in D form can of course be generalized to preparation of any enantiomeric mixture, in particular the racemate.

WORKING EXAMPLES

EXAMPLE 1

Preparation of an intermediate

Step 1

1,3:2,5:4,6-Tri-O-methylene-D-mannitol

In a 2 l round-bottomed flask were introduced 250 g (1.37 mol) of D-mannitol and 500 ml of 37% formaldehyde in water solution. With stirring, 500 ml of conc. hydrochloric acid was added. A clear solution was obtained, which was kept at 45°–50° C. for 120 h. The solution soon started to deposit colourless crystals, the amount of which gradually increased. As soon as the mannitol had dissolved, the stirring was interrupted in order to obtain large crystals. After the stipulated time, the mixture was cooled to 10° C. and filtered with due precaution (mixtures of formaldehyde and hydrochloric acid should be treated as carcinogenic), and the crystals were washed with ice-water and 5% sodium carbonate solution until free from acid. Drying at room temperature gave 281.5 g (1.29 mol, 94%) of material melting at 230°–232° C. $^1$H NMR (90 MHz, CDCl$_3$): $\delta$3.32–3.85 (m, 6H), 4.10–4.35 (m, 2H), 4.64 (d, 2H, J 7 Hz), 4.85 (s, 2 H), 5.12 (d, 2H, J 7 Hz).

Step 2

1,6-Di-O-acetyl-3,4-bis-O-(acetoxymethyl)-2,5-O-methylene-D-mannitol

An acetylation reagent was prepared from 280 ml of acetic anhydride, 120 ml of glacial acetic acid, and 4 ml of conc. sulfuric acid. To this stirred mixture, cooled in an ice-bath, was added 80 g (0.367 mol) of 1,3:2,5:4,6-tri-O-methylene-D-mannitol in finely powdered form, and the external cooling bath was removed. After 20–25 min, all solid material had dissolved, but soon (5 min), crystals started to appear. After another 10 min, the entire reaction mixture was stirred into 3 l of ice-water, and the resulting suspension was left overnight at 5° C. The crystals were collected on a suction filter, washed with cold, saturated sodium bicarbonate solution and water, and dried. Recrystallization from 1 of 95% ethanol gave 98.2 g (63%), m.p. 126°–127° C. $^1$H NMR (90 MHz, CDCl$_3$): $\delta$2.10 (s, 6H), 2.14 (s, 6H), 3.60–3.95 (m, 4H), 4.05–4.50 (m, 4H), 4.80 (s, 2H), 5.24 (d, 2H, J 7 Hz), 5.60 (d, 2H, J 7 Hz).

Note: The recrystallization step may be omitted, since it diminishes the yield by 10–15%. The subsequent step may be carried out with non-recrystallized material.

Step 3

2,5-O-Methylene-D-mannitol

Of the preceding compound, 1,6-di-O-acetyl-3,4-bis-0-(acetoxymethyl)--2,5-O-methylene-D-mannitol, 40 g (0.095 mol) was dissolved in 400 ml of chloroform, and the solution was cooled to 5° C. 40 ml of a 0.2 M solution of sodium methoxide in methanol, was added, and the mixture was kept overnight at 5° C. The resulting colourless crystals were filtered off, washed with chloroform, and dried. Yield 18.45 g (100%), m.p. 169°–171° C. The 90 MHz

Step 4

2,5-O-Methylene-1,6-di-O-p-toluenesulfonyl-D-mannitol

A solution of 35.65 g (0.187 mol) of p-toluenesulfonyl chloride in 70 ml of dry pyridine was added during 30 min while stirring to a solution of 17.8 g (0.092 mol) of 2,5-O-methylene-D-mannitol in 180 ml of dry pyridine, the temperature being kept at 0° C. The mixture was left overnight at room temperature, and as much as possible of the solvent was removed at reduced pressure, the bath temperature not exceeding 40° C. The remaining oil was poured into 1.5 l of ice-water and stirred until it became crystalline. The crude product was collected on a suction filter, washed with cold water, and recrystallized from 700 ml of methanol to yield 29.9 g, m.p. 146°–147° C. Partial evaporation of the mother liquor gave a second crop of 3.6 g, m.p. 143°–144° C., combined yield 73%. $^1$H NMR (90 MHz, CDCl$_3$): $\delta$2 47 (s, 6H), 3.12 (broad s, 2H), 3.38–3.90 (m, 4H), 4.33 (d, 4H, J 5 Hz), 4.65 (s, 2H), 7.40 (d, 4H, J 9 Hz), 7.90 (d, 4H, J 9 Hz).

Step 5

2,5-O-Methylene-3,4-O-methoxymethylene-1,6-di-O-p-toluene-sulfonyl-D-mannitol A solution of 10 g (0.02 mol) of 2,5-O-methylene-1,6-di-O-p-toluenesul-fonyl-D-mannitol in 50 ml (0.45 mol) of trimethyl orthoformate was treated with 25 mg of p-toluenesulfonic acid. After 5 h at room temperature, it was evaporated at reduced pressure to remove methanol and most of the excess orthoformate (which can be recovered) and again treated with 50 ml of trimethyl orthoformate overnight. After neutralization with about 250 mg of solid potassium carbonate (stirring for 1 h), it was filtered and evaporated to dryness. A 100% yield, 10.9 g, of a crystalline product, m.p. 124°–127° C., was obtained. $^1$H NMR (90 MHz, CDCl$_3$): $\delta$2.45 (s, 6H), 3.32 (s, 3H), 3.70–4.40 (m, 8H), 4.76 (s, 2H), 5.78 (s, 1H), 7.40 (d, 4H, J 9 Hz), 7.90 (d, 4H, J 9 Hz).

Step 6

1,6-Bis-O-p-(2-methoxyethyl)phenyl-3,4-O--methxymethylene-2,5-O-methylene-D-mannitol A solution of 2.28 g (15 mmol) of p-(2-methoxyethyl)-phenol in 5 ml of acetonitrile was treated with 0.99 g (15 mmol, assuming 85%) of potassium hydroxide dissolved in the minimum amount of water. Of the preceding protected ditosylate, 2,72 g (5 mmol) was added, and the mixture was refluxed for 48 h. Crystals, probably consisting of potassium p-toluenesulfonate, started to appear already during the first hour. The solvent was removed at reduced pressure, and the residue was distributed between ether and water. The ether phase was washed three times with 2 M sodium hydroxide solution, dried over sodium sulfate, filtered and evaporated. The yield was 2.30 g (91%). An analytical sample, recrystallized from an ether-pentane mixture, had m.p. 90°–91° C. $^1$H NMR (90 MHz, CDCl$_3$): $\delta$2.83 (t, 4H, J 7 Hz), 3.38 (s, 9H), 3.58 (t, 4H, J 7 Hz), 3.85–4.65 (m, 8H), 5.17 (s, 2H), 5.88 (s, 1H), 6.95 (d, 4H, J 10 Hz), 7.22 (d, 4H, J 10 Hz).

Note: The reaction time has not been optimized. Runs during 72 h have given higher yield. The compound is poorly soluble in ether. Workup with 2:1 ether-dichloromethane is easier.

Step 7

1,6-Bis-O-p-(2-methoxyethyl)phenyl-2,5-O-methylene-D-mannitol

Of the preceding compound, 2.38 g (4.7 mmol) was dissolved in 10 ml of formic acid and 10 ml of water. The mixture was stirred overnight and the solvent was removed at reduced pressure. The residue was dissolved in methanol, and the pH value brought to 9 with 10 M sodium hydroxide solution. Water was added in small portions until a crystalline precipitate started to form, and the solution was cooled to 5° C. The crystals were filtered off and washed with water. There was obtained 1.62 g (75%) of needles, m.p. 98° C. 1H NMR (90 MHz, CDCl$_3$): $\delta$2.83 (t, 4H, J 7 Hz), 3.38 (s, 6H), 3.58 (t, 4H, J 7 Hz), 3.70–4.40 (m, 8H), 4.92 (s, 2H), 6.95 (d, 4H, J 10 Hz), 7.22 (d, 4H, J 10 Hz). The remaining OH protons were hidden under other signals but occur according to the integral in the region 2.7–3.0.

Note: Recrystallization from diisopropyl ether - ethyl acetate on a larger batch produced material with m.p. 98°14 99° C. The synthetic sequence starting with 2,5-O-methylene-1,6-di-O-p-toluenesulfonyl-D-mannitol and involving protection of the 3 and 4 hydroxy groups, nucleophilic substitution at positions 1 and 6, and hydrolysis of the methoxymethylene protective group can be carried out without recrystallization of the intermediates. The overall yield of these three steps is then 73%.

EXAMPLE 2

Preparation of an end compound

Step 1

2,2'-O-Methylenebis[3-O-p-(2-methoxyethyl)phenyl-(R)-glyceraldehyde]

A solution of 2.12 g (4.3 mmol, assuming 90% content) of lead tetraacetate in 25 ml of dichloromethane was cooled in an ice-bath to 5°–10° C., and 2.0 g (4.3 mmol) of 1,6-Bis-O-p-(2-methoxyethyl)phenyl-2,5-O-methylene-D-mannitol was added. The mixture was kept at ice-bath temperature for 1 h and at room temperature for 1 h. It was filtered to remove insoluble lead diacetate and washed three times with water to remove acetic acid. Drying over sodium sulfate followed by filtration and evaporation gave 1.91 g (96.5%) of a yellowish oil. $^1$H NMR (90 MHz, CDCl$_3$): $\delta$2.83 (t, 4H, J 7 Hz), 3.38 (s, 6H), 3.58 (t, 4H, J 7 Hz), 4.20–4.38 (m, 4H), 4.50–4.66 (m, 2H), 5.18 (s, 2H), 6.86 (d, 4H, J 9 Hz), 7.20 (d, 4H, J 9 Hz), 9.91 (s, 2H). The compound was used in the next step without undue delay.

Step 2

2,2'-O-Methylenebis(S)-1-O-p-(2-methoxyethyl)phenyl-glycerol]

A solution of 3.44 g (15 mmol) of ethyltributylammonium borohydride in 50 ml of dichloromethane was treated with 2.4 ml (30 mmol) of 1,2-dichloroethane under nitrogen. A preparation of 15 mmol of 2,2'-O-methylenebis3-O-p-(2-methoxyethyl)phenyl-(R)glyceraldehyde]had been prepared as described in the preceding description; the dried solution had a volume of 50 ml. The dialdehyde solution was added to the diborane solution 15 min after the 1,2-dichloroethane addition, and the reaction mixture was left with stirring overnight. The excess diborane was decomposed through addition of 10 ml of acetone. After 1 h of stirring, the reaction mixture was washed with water to remove the quaternary ammonium chloride, and stirred with 50 ml of 2 M sodium hydroxide solution for 1 h. The organic phase was separated and dried over sodium sulfate, filtered and evaporated to yield an oil (7.5 g, more than the stoichiometric amount because of contaminants). It was not further purified but used directly in the next step. $^1$H NMR (90 MHz, CDCl$_3$): δ2.83 (t, 4H, J 7 Hz), 3.38 (s, 6H), 3.60 (t, 4H, J 7 Hz), 3.70–4.15 (m, 12H), 5.08 (s, 2H), 6.86 (d, 4H, J 9 Hz), 7.20 (d, 4H, J 9 Hz).

Step 3

2,2'-O-Methylenebis(R)-1-O-methanesulfonyl-3-O-p(2-methoxyethyl)phenylglycerol]

The entire 15 mmol batch of the preceding diol was dissolved in 60 ml of dichloromethane, and 4.55 g (45 mmol) of triethylamine was added. At 0°–10° C., 3.78 g (33 mmol) of methanesulfonyl chloride was carefully added; the mixture was left 1 h in an ice-bath and 1 h at room temperature. It was washed twice with 1 M hydrochloric acid (50+50 ml) to remove triethylamine, dried over sodium sulfate, filtered and evaporated. A yellow oil, 9.38 g, was obtained. Chromatography (silica gel/ethyl acetate) of 460 mg of this oil gave 400 mg of a colourless product. The yield can thus be calculated to 87%. $^1$H NMR (90 MHz, CDCl$_3$): δ2.83 (t, 4H, J 7 Hz), 3.05 (s, 6H), 3.38 (s, 6H), 3.60 (t, 4H, J 7 Hz), 4.03–4.63 (m, 10H), 5.08 (s, 2H), 6.86 (d, 4H, J 9 Hz), 7.20 (d, 4H, J 9 Hz).

The following step, deprotection of the acetal bridge, was performed on the crude product.

Step 4

2,2'-Methylenedioxybis(S)-N-isopropyl-3-p-(2-methoxyethyl)phenoxypropylamine]

Of the dimesylated acetal, 2,2'-O-methylenebis(R)-1-O-methanesulfonyl--3-O-p(2-methoxyethyl)phenylglycerol], 931 mg (1.5 mmol) was refluxed in 5 ml of isopropylamine for 4 days, inevitable loss of amine being replaced at intervals. The reaction mixture was distributed between dichloromethane and 2 M sodium hydroxide solution, and the organic phase washed with water, dried over sodium sulfate, filtered and evaporated. There was obtained 770 mg (94%) of an oil, $^1$H NMR (90 MHz, CDCl$_3$): δ1.03 (d, 12H, J 7 Hz), 2.6–3.0 (m, 12H), 3.38 (s, 6H), 3.60 (t, 4H, J 7 Hz), 3.9–4.2 (m, 6H), 5.05 (s, 2H), 6.86 (d, 4H, J 9 Hz), 7.17 (d, 4H, J 9 Hz).

Step 5

(S)-1-Isopropylamino-3-p-(2-methoxyethyl)phenoxypropan-2-ol

Of the protected (acetal-bridged) diamine, 1.79 g was refluxed with a solution of 2 ml of conc. sulfuric acid in 20 ml of methanol overnight. The reaction mixture was diluted with water and the methanol was evaporated at reduced pressure. Neutral impurities were removed by extraction with dichloromethane, and the water phase was made alkaline with 10 M sodium hydroxide solution. The liberated amine was extracted into dichloromethane, and the solution was dried and evaporated. The title compound was obtained as a crystallizing oil, 1.65 g (93%). The $^1$H NMR spectrum was identical to that of authentic metoprolol; (90 MHz, CDCl$_3$) δ1.06 (d, 6H, J 7 Hz), 2.3 (1H, broad), 2.83 (t, 2H, J 7 Hz), 2.65–3.00 (3H, m), 3.38 (s, 3H), 3.60 (t, 2H, J 7 Hz), 3.88–4.10 (3H, m), 6.89 (d, 2H, J 9 Hz), 7.22 (d, 2H, J 9 Hz).

The enantiomeric purity was determined via derivatization with O-methylmandelic acid chloride and HPLC of the diastereomeric amides to >99.3% (ee).

EXAMPLE 3.

Alternative route to steps 4 and 5 in Example 2.

Step 4

(R)-1-O-Methanesulfonyl-3-O-p-(2-methoxyethyl)-phenylglycerol

Of the dimesylated acetal, 8 g (12.8 mmol) was dissolved in a mixture of 50 ml of methanol and 5 ml of conc. sulfuric acid. The progress of the reaction was followed by TLC (SiO$_2$, 5% CH$_3$OH in CH$_2$Cl$_2$). The half-life of the reaction at room temperature was of the order of 24 h. After 4 days, the reaction mixture was diluted with twice its volume of water, the methanol was evaporated at reduced pressure, and the reaction product extracted into dichloromethane. Sulfuric acid was removed by washing with water until neutral, and the solution was dried and evaporated to yield 6.57 g (96%) of a yellowish oil. $^1$H NMR (90 MHz, CDCl$_3$) δ2.83 (t, 2H, J 7 Hz, superimposed on 1H, broad), 3.05 (s, 3H), 3.38 (s, 3H), 3.60 (t, 2H, J 7 Hz), 4.00–4.10 (m, 2H), 4.20–4.50 (m, 3H), 6.89 (d, 2H, J 9 Hz), 7.22 (d, 2H, J 9 Hz).

Step 5

(S)-1-Isopropylamino-3-p-(2-methoxyethyl)phenoxypropan-2-ol

A solution of 4.57 g (15 mmol) of (R)-1-O-methanesulfonyl-3-O-p-(2-methoxyethyl)phenylglycerol in 25 ml of isopropylamine was refluxed overnight. After evaporation of excess isopropylamine, the remainder was dissolved in 1 M sulfuric acid, neutral compounds were removed by a dichloromethane wash, and the solution was brought to pH 14 with 10 M sodium hydroxide. The amine was extracted into dichloromethane (four extractions), and the solution was dried and evaporated to yield 3.1 g (77%) of the title amine. The material was found to have an optical purity of at least 99%.

EXAMPLE 4

Preparation of an intermediate

Steps 1–3

These steps were identical to steps 1–3 of Example 1.

Step 4

1,6-Di-O-p-bromobenzenesulfonyl-2,5-O-methylene-D-mannitol

A solution of 1.94 g (10 mmol) of 2,5-O-methylene-D-mannitol in 20 ml of dry pyridine was cooled to 0° C. and treated dropwise with a solution of 5.24 g (20.5 mmol) of p-bromobenzenesulfonyl chloride in 10 ml of dry pyridine. The reaction mixture was left at room temperature overnight, evaporated at reduced pressure to remove as much as possible of the pyridine, and triturated with ice water. A crystalline mass was obtained which was filtered off, washed with water and recrystallized from ethanol to give 1.65 g of colourless crystals, m.p. 149°–149.5° C. From the mother liquor, a second crop was secured, m.p. 148°–149° C.; combined yield 41%.

Step 5

1,6-Di-O-p-bromobenzenesulfonyl-3,4-O-(1-methoxyethylidene)-2,5-O-methylene-D-mannitol A solution of 20.8 g (32.9 mmol) of 1,6-di-O-p-bromobenzenesulfonyl-2,5-O-methylene-D-mannitol in 250 ml of trimethyl orthoacetate was treated with 60 mg of p-toluenesulfonic acid and left overnight at room temperature. Enough solid potassium carbonate to neutralize the catalyst was added, and volatile material was removed by evaporation at reduced pressure. The theoretical quantity of a coulorless, low-melting solid was obtained. $^1$H NMR (90 MHz, CDCl$_3$): δ1.47 (s, 3H), 3.27 (s, 3H), 3.70–4.40 (m, 8H), 4.80 (s, 2H), 7.70–7.92 (m, 8H).

Step 6

1,6-Bis-O-p-(2-cyclopropylmethoxyethoxy)phenyl-3,4-O-(1-methoxyethylidene)-2,5-O-methylene-D-mannitol A mixture of 20.3 g (30 mmol) of 1,6-di-O-p-bromobenzenesulfonyl-3,4-O-(1-methoxyethylidene)-2,5-O-methylene-D-mannitol, 13 g (60 mmol) of p-(2-cyclopropylmethoxyethoxyphenol, 7.9 g (70 mmol) of dry potassium carbonate and 150 ml of acetonitrile was refluxed and stirred for 48 h, filtered and evaporated at reduced pressure. The remaining oil was dissolved in ether and washed twice with 2 M sodium hydroxide, dried and evaporated to yield 19 g (100%) of an oil. The 90 MHz $^1$H NMR spectrum was in agreement with the proposed structure.

Step 7

1,6-Bis-O-p-(2-cyclopropylmethoxyethoxy)phenyl-2,5-O-methylene-D-mannitol

A solution of 19 g (30 mmol) of 1,6-Bis-O-p-(2-cyclopropylmethoxy- ethoxy)phenyl-3,4-O-(1-methoxyethylidene)-2,5-O-methylene-D-mannitol in 25 ml of anhydrous formic acid and 12.5 ml of water was left at room temperature for 1 h. It was evaporated at reduced pressure and dissolved in 100 ml of methanol. The pH value was brought to 11 by the addition of 10 M sodium hydroxide, and the mixture was stirred at 65° C. for 20 h. After evaporation of the solvent, the residue was recrystallized from 95% ethanol to give 10.6 g (62%) of colourless crystals, m.p. 108° C. $^1$H NMR (90 MHz, CDCl$_3$): δ0.25–0.45 (m, 4H), 0.55–0.80 (m, 4H), 1.05–1.40 (m, 2H), 2.55 (s, broad, 2H), 3.50 (d, 4H, J 7 Hz), 3.80–4.45 (m, 16H), 5.05 (s, 2H), 7.03 (s, 8H).

EXAMPLE 5

Preparation of an end compound

Step 1

2,2'-O-Methylenebis3-O-p-(2-cyclopropylmethoxyethoxy)phenyl-(R)glyceraldehyde]

A stirred solution of 9.11 g (18.5 mmol, assuming 90% content) of lead tetraacetate in 100 ml of dichloromethane was treated with 10.6 g (18.45 mmol) of 1,6-bis-O-p-(2-cyclopropylmethoxyethoxy)phenyl--2,5-O-methylene-D-mannitol. After 30 min, the precipitate, consisting of lead diacetate, was filtered off and the filtrate was washed with water, filtered to remove a trace of lead dioxide, dried and evaporated at reduced pressure. An oil was obtained which was used directly in the following step. $^1$H NMR (90 MHz, CDCl$_3$): δ0.25–0.45 (m, 4H), 0.55–0.80 (m, 4H), 1.05–1.40 (m, 2H), 3.50 (d, 4H, J 7 Hz), 3.80–4.40 (m, 12H), 4.55–4.75 (m, 2H), 5.22 (s, 2H), 6.97 (s, 8H), 9.90 (s, 2H).

Step 2

2,2'-O-Methylenebis[(S)-1-O-p-(2-cyclopropylmethoxyethoxy)phenylglycerol

A solution of 4.9 g (19 mmol) of tetrabutylammonium borohydride in 75 ml of dichloromethane was treated with 3 ml (38 mmol) of 1,2-dichloroethane and refluxed for 15 min. The entire amount of oil from Step 1 (max 18.5 mmol) was dissolved in 25 ml of dichloromethane and added dropwise under nitrogen. The stirring was continued at room temperature overnight. After destruction of excess diborane with 2 M acetic acid, the solution was washed three times with water, stirred for 90 min with 100 ml of 2 M sodium hydroxide, dried and evaporated at reduced pressure. Purification via chromotography on a silica gel column (Merck 0.063–0.200 mm, length 600 mm, diam. 50 mm) using 5% methanol in dichloromethane as the eluant yielded a pure fraction weighing 5.4 g (50% yield for two steps), m.p. 80°–83° C. $^1$H NMR (90 MHz, CDCl$_3$): δ0.25–0.45 (m, 4H), 0.55–0.80 (m, 4H), 1.05–1.40 (m, 2H), 3.0 (s, broad, 2H), 3.50 (d, 4H, J 7 Hz), 3.80–4.30 (m, 18H), 5.15 (s, 2H), 6.98 (s, 8H).

Step 3

2,2'-O-Methylenebis[(R)-1-O-methanesulfonyl-3-O-p-(2-cyclopropylmethoxyethoxy)phenylglycerol]

A solution of 5.9 g (10.2 mmol) of the preceding dialcohol and 3.10 g (31 mmol) of triethylamine in 50 ml of dichloromethane was treated dropwise with a solution of 2.58 g (22.5 mmol) of methanesulfonyl chloride in 10 ml of dichloromethane at 0°–5° C. After 30 min at this temperature and 1 h at room temperature, the solution was washed twice with ice-cold 1 M hydrochloric acid followed by water, dried over sodium sulfate, filtered and evaporated to yield 6.63 g (88%) of an oil. $^1$H NMR (90 MHz, CDCl$_3$): δ0.25–0.45 (m, 4H), 0.55–0.80 (m, 4H), 1.05–1.40 (m, 2H), 3.18 (s, 6H), 3.50 (d, 4H, J 7 Hz), 3.80–4.70 (m, 18H), 5.15 (s, 2H), 6.98 (s, 8H).

Step 4

(R)-1-O-Methanesulfonyl-3-O-p-(2-cyclopropylmethoxyethoxy)phenylglycerol

Of the preceding acetal, 6.3 g (8.6 mmol) was stirred for 5 days at room temperature with 6 ml of conc. sulfuric acid in 75 ml of methanol. After addition of 100 ml of water, the methanol was removed at reduced pressure, and the residue was extracted three times with dichloromethane. The combined extracts were washed with water, dried and evaporated at reduced pressure to yield 5.56 g (15.4 mmol, 90%) of an oil. $^1$H NMR (90 MHz, CDCl$_3$): δ0.25–0.45 (m, 2H), 0.55–0.80 (m, 2H), 1.05–1.40 (m, 1H), 2.50 (s, broad, 1H), 3.13 (s, 3H), 3.45 (d, 2H, J 7 Hz), 3.80–4.55 (m, 9H), 6.98 (s, 4H).

Step 5

N-[2-[[(S)-2-Hydroxy-3-[4-(2-cyclopropylmethoxyethoxy)phenoxy]propyl]amino]ethyl]-4-morpholinecarboxamide A solution of 1.47 g (7 mmol) of N-(2-aminoethyl)-4-morpholinecarboxamide hydrochloride in 15 ml of absolute ethanol was treated with the equivalent amount of 10 M sodium hydroxide to liberate the free amine. A solution of 1.26 g (3.5 mmol) of (R)-1-O-methanesulfonyl-3-O-p-(2-cyclopropylmethoxyethoxy)phenylglycerol in 15 ml of absolute ethanol was added, and the mixture was stirred at 45° C. for 2 days. Precipitated salts were filtered off, and the solvent was removed at reduced pressure. The residue was partitioned between dichloromethane and an aqueous buffer at pH 10. The organic phase was extracted with aqueous sulfuric acid, final pH value 3, to convert the amine to salt. After washing the aqueous phase with ethyl acetate the pH value was increased to 10 and the liberated base taken up in dichloromethane. Evaporation and recrystallization of the residue from ethyl acetate gave 0.7 g (46%) of colourless crystals, m.p. 80°–81° C. The enantiomeric purity was determined via derivatization with O-methylmandelic acid chloride and HPLC of the diastereomeric amides to better than 99%.(ee). The 1H and 13C NMR spectra were identical to those of authentic, racemic material. 13C NMR (20 MHz, CDCl3) δ(ref. to TMS): 3.1, 10.6, 40.3, 44.0, 49,4, 51.9, 66.5, 68.2, 68.5, 69.0, 71.3, 76.2, 115.5, 115.8, 152.9, 153.4, 158.3, 189.2, (proton noise dec.).

I claim:

1. A process for the preparation of an aryloxypropanolamine of the formula

Ar-OCH₂CH(OH)CH₂NH-R    I or an acid addition salt thereof, wherein Ar is a carbocyclic or heterocyclic aromatic group and R is an alkyl or substituted alkyl group having 1 to 6 carbon atoms, characterized in subjecting a compound of the formula

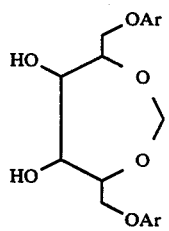

II to oxidative cleavage to form a dialdehyde of the formula

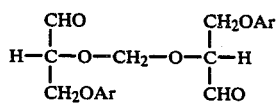

III which is then made subject to reduction, amination and hydrolysis, by the following sequence of steps

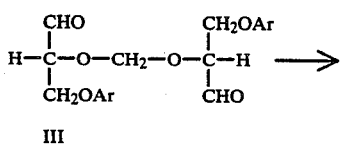

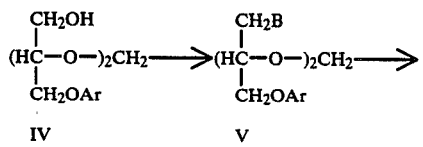

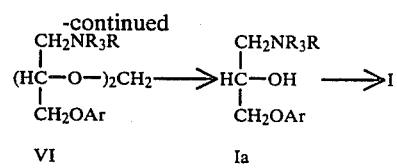

wherein B is a leaving group, R₃ is hydrogen or a nitrogen protective group and R and Ar are as defined above, and when R₃ is a nitrogen protective group, removal of said group R₃.

2. A process according to claim 1 characterized in employing an enantiomerically substantially pure compound of formula II to produce the compound of formula I as a substantially pure enantiomer.

3. A process according to claim 1 characterized in using the compound of formula II as the D isomer, to produce the compound of formula I in S form.

4. A process for the preparation of an aryloxypropanolamine of the formula

Ar-OCH₂CH(OH)CH₂NH-R    I or an acid addition salt thereof, wherein Ar is a carbocyclic or heterocyclic aromatic group and R is an alkyl or substituted alkyl group having 1 to 6 carbon atoms, characterized in subjecting a compound of the formula

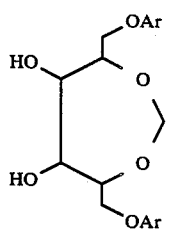

II to oxidative cleavage to form a dialdehyde of the formula

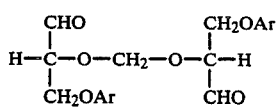

III which is then made subject to reduction, hydrolysis and amination, by the following sequence of steps

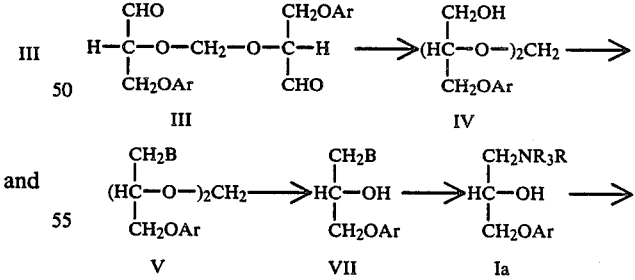

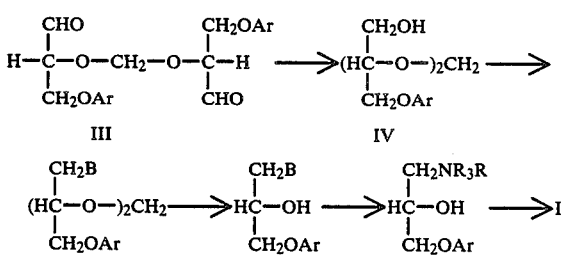

wherein B is a leaving group, R₃ is hydrogen or a nitrogen protective group and R and Ar are as defined above, and when R₃ is a nitrogen protective group, removal of said group R₃.

5. A process according to claim 4 characterized in employing an enantiomerically substantially pure compound of the formula II to produce the compound of formula I as a substantially pure enantiomer.

6. A process according to claim 4, characterized in using the compound of formula II as the D isomer, to produce the compound of formula I in S form.

* * * * *